United States Patent [19]

Tamm et al.

[11] Patent Number: 4,834,536
[45] Date of Patent: May 30, 1989

[54] ELECTRICAL CONTACTS FOR SUPPLYING HEATING CURRENT TO AN ELECTROTHERMAL ATOMIZER

[75] Inventors: Rolf Tamm, Salem; Gerhard Christian, Owingen, both of Fed. Rep. of Germany

[73] Assignee: Bodenseewerk Perkin-Elmer & Co., GmbH, Überlingen, Fed. Rep. of Germany

[21] Appl. No.: 230,405

[22] Filed: Aug. 9, 1988

[30] Foreign Application Priority Data

Aug. 10, 1987 [DE] Fed. Rep. of Germany ....... 3726533

[51] Int. Cl.⁴ ............................................. G01J 21/74
[52] U.S. Cl. .................................... 356/312; 356/244
[58] Field of Search .............................. 356/312, 244

[56] References Cited

U.S. PATENT DOCUMENTS

4,726,678 2/1988 Hütsch et al. ................. 356/312 X

Primary Examiner—F. L. Evans
Attorney, Agent, or Firm—Ronald G. Cummings; Francis L. Masselle; Edwin T. Grimes

[57] ABSTRACT

Electrical contact members 20, 22 for supplying transverse electrical current to a tubular furnace member (22) for electrothermal atomization of samples for analysis by atomic absorption spectrophotometry, the tubular furnace member having diametrically opposite, longitudinally-extending contact ribs (84, 86). The contact members (20, 22) form, in operative assembly, a cavity 88 in which tubular furnace member (24) is accommodated and is held between V-shaped channels (44, 76) in contact members (20, 22). Cavity 88 is formed by a recess (36) in one contact member (20) and covered, except for a separating gap, by the other contact member (22). Respective inert protective gas passages (62, 82) terminate at one end in channels 44, 76.

11 Claims, 6 Drawing Sheets

ELECTRICAL CONTACTS FOR SUPPLYING HEATING CURRENT TO AN ELECTROTHERMAL ATOMIZER

This invention relates generally to electrothermal atomizers for use in flameless atomic absorption spectrophotometry and, particularly, to electrical contacts for supplying heating current to such atomizers.

BACKGROUND AND SUMMARY OF THE INVENTION

Electrothermal atomizers, commonly referred to as heated graphite atomizers or graphite furnaces, are utilized in atomic absorption spectrophotometers for rendering the sample to be analyzed in atomic form. Typically, the furnaces comprise a tubular graphite member clamped between annular graphite contacts, or electrodes, engaging its respective ends. A radial aperture in the side wall of the tubular member at the midpoint of its length serves as a sample port, accommodating the insertion into the tubular member of the substance to be analyzed.

The contacts, usually mounted in cooling jackets, are pressed into tight engagement with the ends of the tubular furnace member by resilient biasing means or a servomotor. An intense electrical current, passed longitudinally through the tubular member between the contacts heats the member to the high temperature required to convert the sample to a "cloud of atoms."

A beam of essentially monochromatic radiation having a wavelength corresponding to a characteristic spectral line of the substance (the "analyte") sought to be determined in the sample undergoing analysis, is passed longitudinally through the tubular member as permitted by the annular configuration of the electrical contacts. The atomic cloud absorbs the radiation in proportion to the concentration of the analyte in the sample; the reduction in intensity of the beam caused by the absorption is determined by a suitable detector and converted into an electrical signal.

In order to prevent rapid deterioration of the tubular graphite member by oxidation at the high temperatures required for atomization of the analyte, provision is made for enveloping it in a flow of inert protective gas.

Due to the heat sink effect of the contacts and their associated cooling jackets, the ends of the tubular member are cooler than the medial portion. This non-uniformity of temperature results in the deposition of sample on the cooler ends of the tubular member; the deposit is re-evaporated in subsequent use of the tubular member, contaminating the new sample.

A graphite furnace of the type described above is shown in U.S. Pat. No. 4,022,530. In this particular furnace, the electrode members are tubular, rather than annular, and coaxially envelopes the tubular graphite furnace member over substantially its entire length, except for a gap between the confronting ends of the electrodes. One of the tubular electrodes extends beyond the mid-point of the furnace member and contains a sidewall aperture registering with, and providing access to, the sample port.

Inert gas is introduced into the ends of the tubular member and flows outwardly through the sample port and the aperture in the tubular electrode aligned therewith.

In one attempt to achieve a more uniform temperature distribution in the tubular member of graphite furnaces it has been proposed to pass the heating current transversely through the furnace member rather than longitudinally. To this end, a contact arrangement is described in U.S. Pat. No. 4,407,582 employing two pairs of interconnected contacts in the form of bifurcated electrode members radially engaging a graphite tube on opposite sides. The heating current flows in the area of the ends in a circumferential direction through the graphite tube, heating it in the area of its ends. Heat flows from the ends to the center, achieving a more uniform temperature distribution.

In this known contact arrangement, the electrodes engage the hot parts of the graphite tube; consequently, the reproducibility of the contact characteristics is poor. Furthermore, it is difficult to protect the graphite tube from exposure to atmospheric oxygen by means of an inert protective gas flow, resulting in short useful life of the graphite tube.

In German Offenlegungsschrift 35 34 017 and the publication in "Analytical Chemistry", 58 (1986), 1973, there is described a graphite furnace in which the tubular furnace member is rectangular in cross-section and has integral contact pieces extending transversely to the axis of the tubular member. Thus, contact is effected in a cold area at plane surfaces. While this contact arrangement avoids the problem of non-reproducible contact characteristics, the difficulty of protecting the furnace from the entrance of air by an inert gas mantle remains.

Consequently, the furnace tube deteriorates rapidly in use and is, therefore, considered an expendable part. As the furnace with its integral contact is a relatively large graphite body, it is difficult to fabricate and, therefore, expensive. The combination of rapid deterioration and high replacement costs leads to a high cost per analysis.

It is the general object of this invention to overcome, or at least mitigate, the shortcomings of prior art graphite furnaces as outlined above.

It is a specific object of the invention to provide a contact arrangement of the above-described type having transverse heating current flow that lends itself to, and facilitates, effective protection of the furnace tube against exposure to atmospheric oxygen.

It is a further object of the invention to apply electric heating current to the furnace tube largely without loss.

Still another object of the invention is to cool the furnace well after each reading and thus to reduce the cooling time required prior to introduction of the next sample.

A further object is the provision of an electrothermal contact assembly in which a graphite component heated to high atomizing temperatures and consequently subject to rapid deterioration is relatively easy to fabricate and thus inexpensive.

To the accomplishment of the foregoing objects and others which will become apparent as this description proceeds, the invention contemplates an electrothermal furnace comprising a generally tubular furnace member having copolanar longitudinally extending contact ribs projecting radially outwardly from its outer surface on diametrically opposite sides. A pair of contact members having respective complementary mating surfaces disposed in confronting relation coact to define a cavity accommodating the furnace member and making electrical contact with the contact ribs of the furnace member when it is inserted in the cavity and the contact members disposed with mating surfaces in confronting relation.

As will be more fully appreciated as this description of exemplary embodiments of the invention proceeds, large contact surrounding the furnace member are provided enabling transmission thereto of a high intensity transverse heating current largely without loss. Enclosed in the cavity, the furnace member can be effectively protected from oxidation by an inert gas flow shielding the surfaces of the furnace from atmospheric oxygen. The configuration of the contact members enables large area surface contact with their cooling jackets inasmuch as this is not determined by integral projections of the furnace. In consequence of the large area surface contact, the furnace contact members and concomitantly the furnace can be rapidly cooled after each measurement. The furnace member itself is small and relatively simple in design and therefore easily and inexpensively fabricated.

Exemplary embodiments of the invention will now be described with continued reference to the following drawings in which like reference numerals denote like parts throughout the several views.

Figure 1:
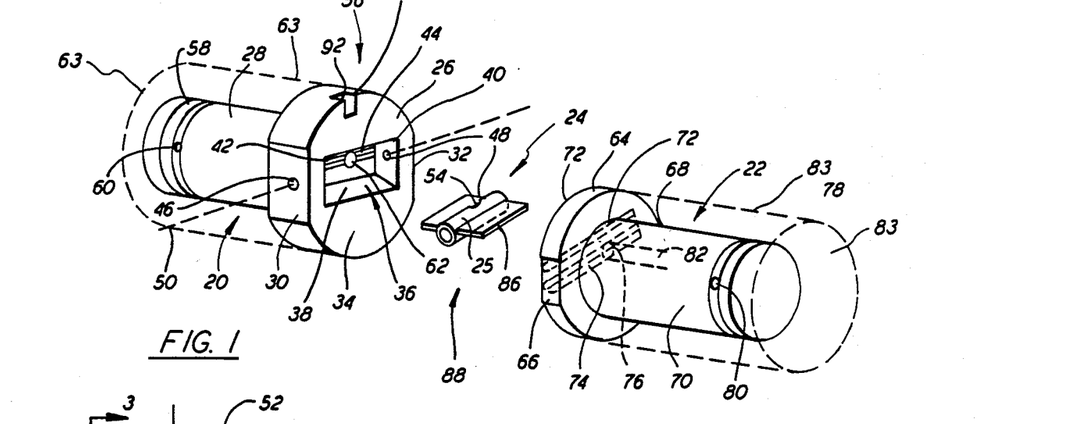
FIG. 1 is an exploded perspective pictorial view of an electrothermal atomization furnace in accordance with the present invention.

Referring now to the drawings and first, in particular, to FIG. 1, there is illustrated an electrothermal atomizing furnace comprising three major components: a first electrical contact member 20; a second electrical contact member 22; and a tubular furnace member 24. All three components would customarily be fabricated of some form of graphite. In the exploded view presented in FIG. 1 the three components are shown in spatial orientation appropriate to their operative assembly with tubular furnace member 24 enclosed between contact members 20, 22.

Contact member 20 has a generally discoid head portion 26 and, coaxially extending from one face thereof, a cylindrical shaft portion 28 of lesser diameter than the head portion. Of generally similar construction is second contact member 22, having a discoid head portion 64 and coaxial cylindrical shaft portion 70. Head portions 26 and 64 have complementary mating surfaces 34 and 35 respectively which are disposed in confronting relation when the contact members 20 and 22 are moved toward each other into operatively assembled position. Discoid head portion 26 of contact member 20 has a substantially greater thickness dimension than its opposite number on contact member 22 and contains in its mating surface 34 a recess 36 in the form of a right rectangular parallelepiped.

Figure 2:
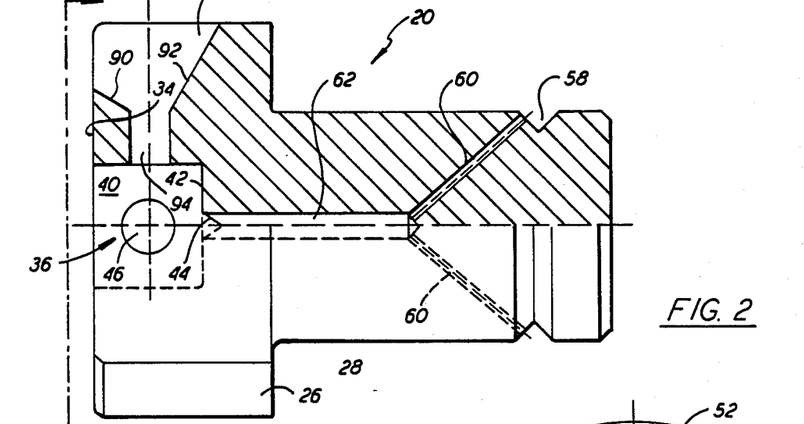
FIG. 2 is a side elevational view, partially in longitudinal section, of a portion of the structure shown in FIG. 1.
Figure 3:
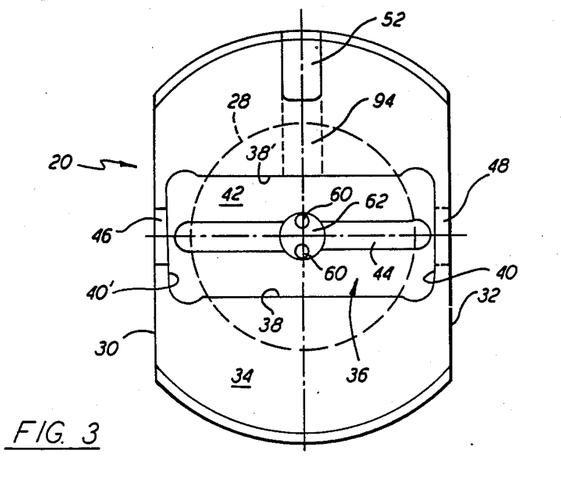
FIG. 3 is an elevational view taken on line 3—3 of FIG. 2.

Recess 36 has longitudinal side wall surfaces 38, 38' which are horizontal as viewed in FIG. 1 and end surfaces 40, 40' (FIGS. 2 and 3). The bottom wall 42 of recess 36 is parallel to mating surface 34 of head 26. Respective flats 30, 32 are provided on opposite sides of the circumferential surface of head portion 26; the flats are parallel to each other and to walls 40, 40' of recess 36.

A channel 44 of V-shaped cross-section and extending parallel to the side walls 38, 38' of recess 36 is formed in bottom wall 42 of the recess. Coaxially aligned bores 46, 48 are provided in the respective end walls 40, 40' of recess 36 extending through to, and opening in, flats 30, 32. Bores 46, 48 accommodate the passage through recess 36 of the spectral radiation beam (represented by broken line 50) which also passes through the tubular furnace member 24 when installed as will be explained presently.

In the uppermost part of the circumferential surface of head 26 as viewed in FIG. 1, a notch 52 is provided which transforms into a vertical, downwardly extending bore (not visible in FIG. 1), as will be explained in greater detail as this description proceeds. In operation the bore is aligned with a sample port 54 of furnace member 24 permitting introduction of a sample as indicated by arrow 56.

Adjacent its distal end, shaft 28 has a circumferential groove 58 which communicates through bores 60 with an inert gas passage 62 extending longitudinally through shaft portion 28 as best appears in FIG. 2. Inert gas passage 62 terminates at the center of V-shaped channel 44.

A cooling jacket 63, symbolically represented in broken line, enables circulation of a cooling medium around contact member 20.

As previously mentioned, contact member 22 is generally similar to contact member 20. Thus, the circumferential surface of its discoid head portion 64 has flats 66, 68 corresponding to 30, 32. Head portion 64, however, is thinner and its mating surface 35 lacks any counterpart of recess 36. Instead, at the corresponding location of recess 36, mating surface 35 has parallel ridges 72, 74 forming a channel 76 of V-shaped cross-section parallel to and correspondingly positioned relative to channel 44 of contact member 20.

As in the case of contact member 20, shaft portion 70 of contact member 22 has a circumferential groove 78 adjacent its distal end. Groove 78 is in flow communication through bores 80 (FIG. 4) with an inert gas passage 82 extending coaxially in shaft 70. Inert gas passage 82 terminates at the midpoint of the V-shaped channel 76.

Figure 4:
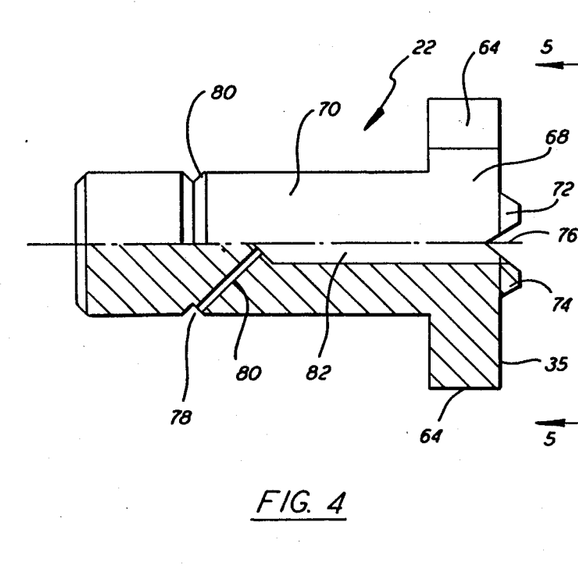
FIG. 4 is a side elevation view, partially in longitudinal section, of another portion of the structure shown in FIG. 1.
Figure 5:
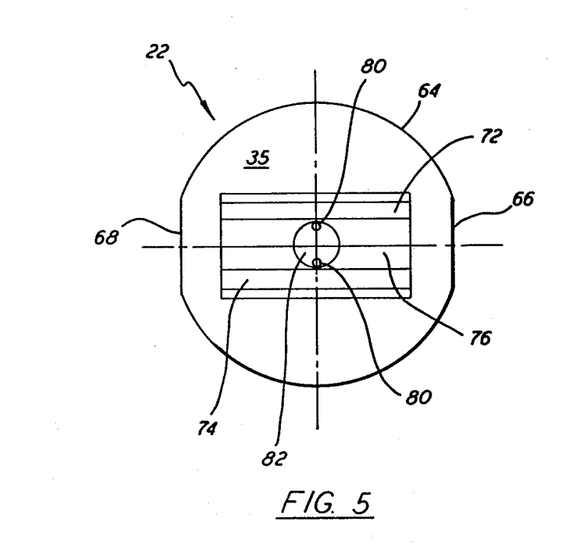
FIG. 5 is an elevational view taken on line 5—5 of FIG. 4.

Like its counterpart 20, contact member 22 is provided with a cooling jacket symbolically shown in broken line at 83.

Figure 6:
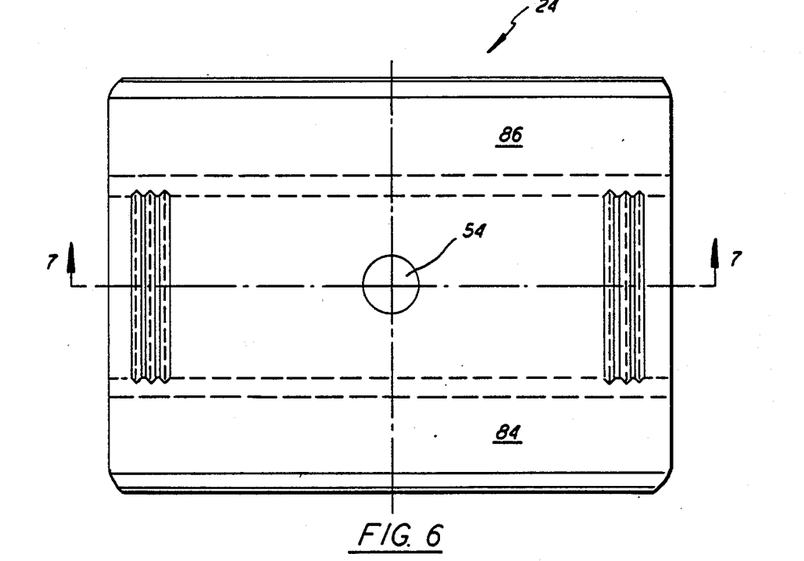
FIG. 6 is a plan view of a third portion of the structure shown in FIG. 1.
Figure 7:
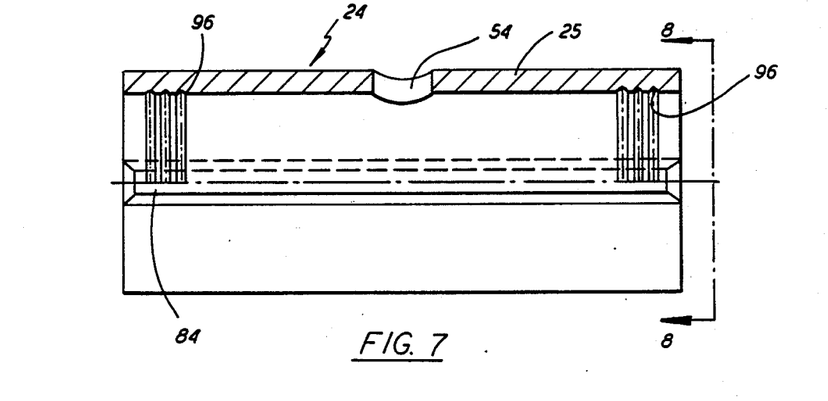
FIG. 7 is a side elevational view, partially in section on line 7—7 of FIG. 6.
Figure 8:
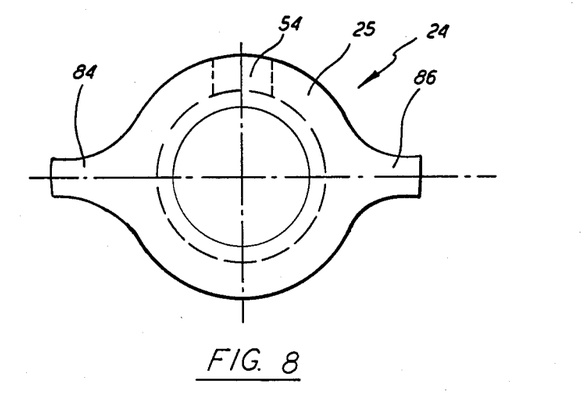
FIG. 8 is an elevational view on line 8—8 of FIG. 7.

Referring to FIGS. 6–8. furnace member 24 has a hollow cylindrical body portion 25 and projecting radially outward from the outer surface of the body portion on diametrically opposite sides, a pair of coplanar electrical contact ribs 84, 86 which extend along the entire length of the cylindrical portion.

In operative assembly, contact members 20 and 22 are disposed with respective mating surfaces 34, 35 in confronting relation, i.e., closely spaced but with a gap between them. Tubular member 24 is disposed within cavity 88, its contact ribs 84, 86 engaging in respective channels 44 and 76, thus establishing a high efficiency electrical connection between the furnace member and contact members 20, 22, which are urged towards one another by a resilient biasing arrangement, a servometer or other suitable means (not shown).

Circumferential grooves 58 and 78 in the respective shaft portions 28 and 70 of contact members 20, 22 register with bores (not shown) in cooling jackets 63, 83, the bores being in flow communication with a source (not shown) of inert protective gas under pressure. From grooves 58, 78 the inert gas flows through bores 60 and 80 (FIGS. 2 and 4) and inert gas passages 62 and 82, respectively, to cavity 88 where it displaces the existing atmosphere and envelops furnace member 24. The inert gas flows out of cavity 88 via existing openings, e.g., 46, 48 and the gap between mating surfaces 34 and 35. Thus, furnace member 24 is continuously immersed in a flow of inert gas which effectively shields it from the ambient atmosphere.

When electrical power is supplied to contact members 20, 22, furnace 24 is heated by electrical current which flows transversely to its longitudinal axis via V-shaped channels 44, 78 and contact ribs 84, 86. As heating is effected substantially uniformly over the entire length of the furnace member, the temperature distribution is likewise substantially uniform over the length of the member.

Due to the large area of surface contact between cooling jackets 63, 83 and shaft portions 28 and 70, contact members 20, 22 are kept cool. When the heating current is discontinued, contact members 20, 22 rapidly absorb and dissipate the heat of furnace member 24. Consequently, after a measurement has been completed, the furnace is relatively quickly ready to receive the next sample.

Referring now to FIGS. 2 and 3 in which contact member 20 is illustrated in greater detail, it will be seen that previously mentioned notch 52 has a funnel shape formed by inclined surfaces 90, 92, as best appears in FIG. 2; these surfaces merge into a downwardly extending vertical bore 94 and facilitate the introduction into sample port 54 of a sampling tube (not shown) e.g., a probe or pipette inserted manually or by means of an automatic sampler such as shown in U.S. Pat. No. 4,111,051.

Referring to FIGS. 6 and 7, the ends of hollow cylindrical furnace body portion 24a are provided with a series of coaxial grooves 96 on their inner surfaces, the purpose of which is to confine the sample, conventionally in liquid form, to the middle region of the furnace tube.

Figure 9:
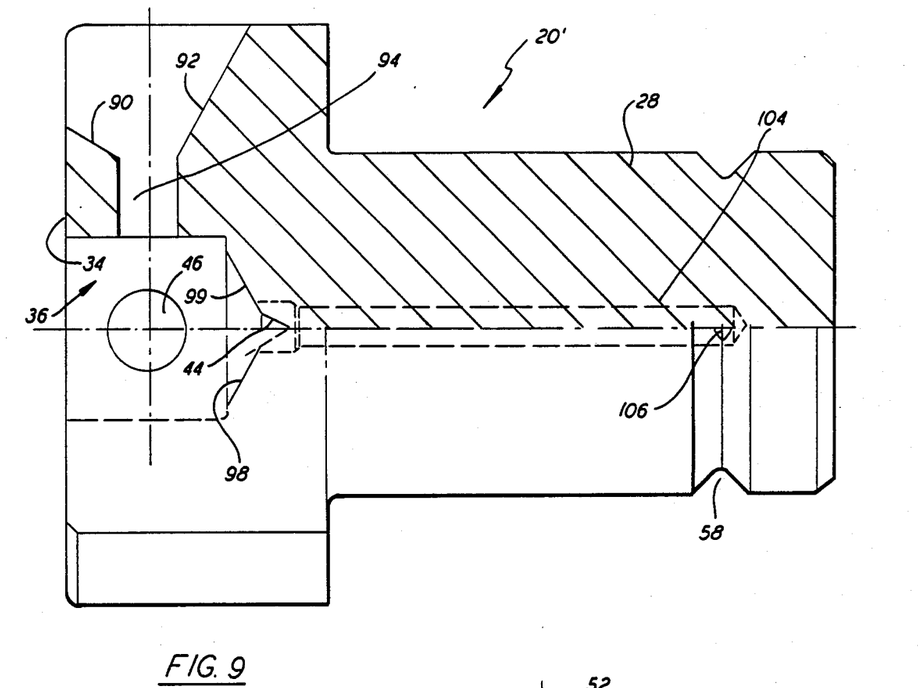
FIG. 9 is a side elevational view comparable to FIG. 2, of a modified embodiment of the invention.
Figure 10:
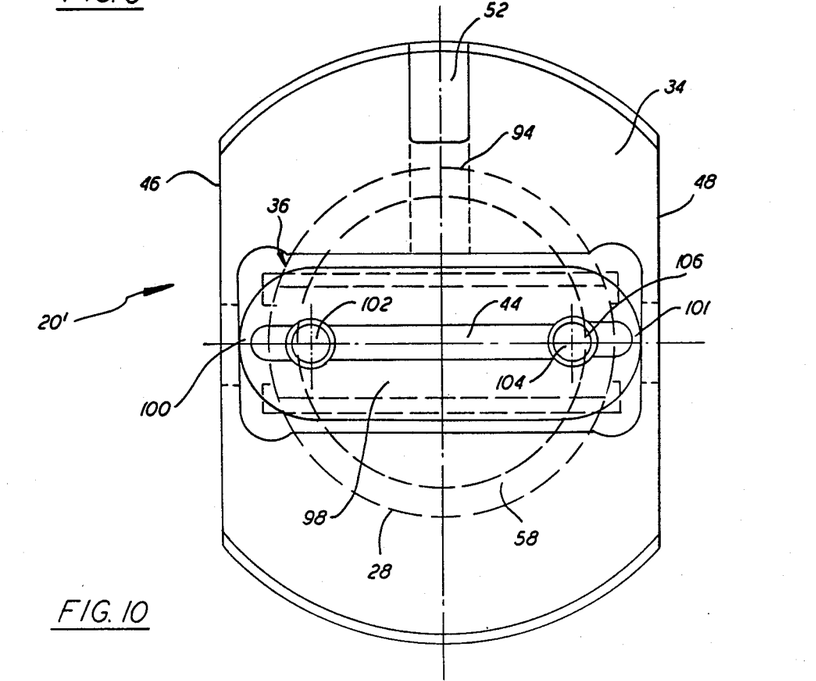
FIG. 10 is an elevational view taken on line 10—10 of FIG. 9.
Figure 11:
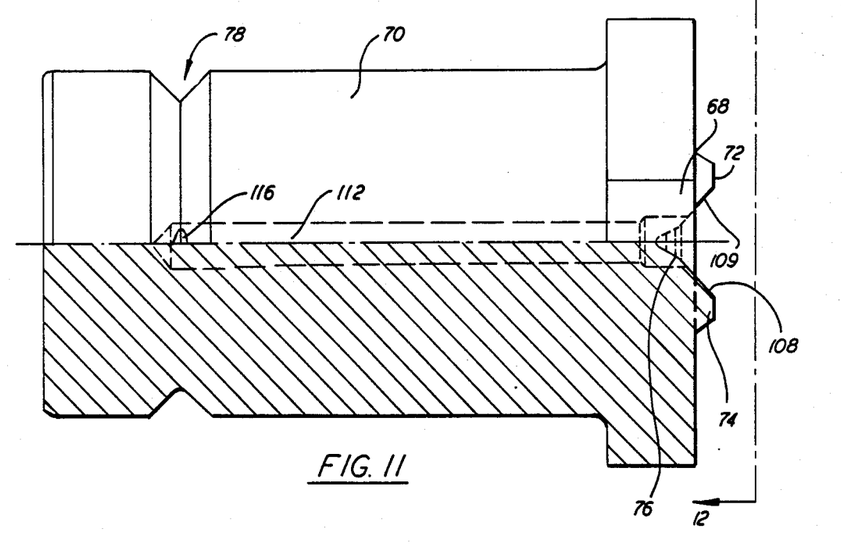
FIG. 11 is a view comparable to FIG. 4 of the modified embodiment of the invention.
Figure 12:
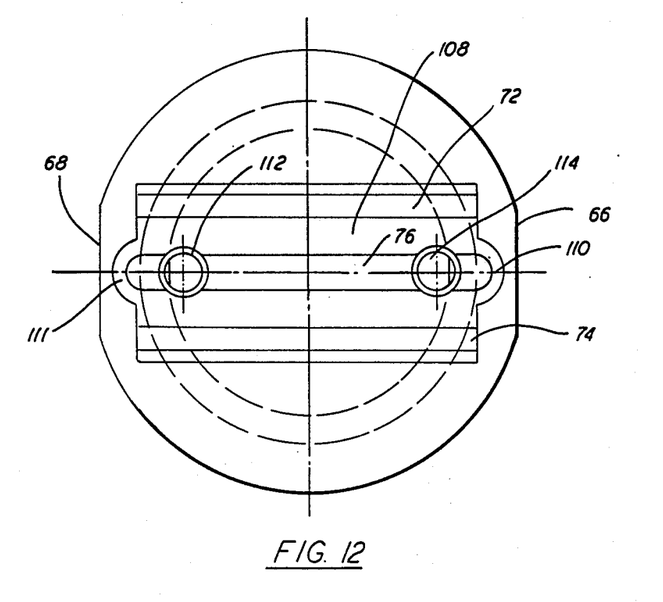
FIG. 12 is an elevational view on line 12—12 of FIG. 11.

A slightly modified form of the invention is shown in FIGS. 9–12. The modified version of contact member 20 is shown in FIGS. 9 and 10 wherein it is designated generally as 20'. In this embodiment, the bottom wall (42 in the first-described embodiment) takes the form of inclined surfaces 98, 99 diverging in the direction of mating surface 34 containing recess 36. In the opposite (converging) direction, surfaces 98, 99 merge with respective walls of V-shaped channel 44 which have a smaller included angle. Similar, inclined surfaces 100, 101 are provided at the respective ends of recess 36 merging with the ends of channel 44. Referring to FIGS. 11 and 12, the corresponding (second) contact member 22, is similarly provided with inclined guiding surfaces 108, 109 merging with V-shaped channel 76 and inclined guiding surfaces 110, 111 merging with the ends of V-shaped channel 76. This construction ensures that furnace member 24 cannot tilt and its contact rib will snap safely and surely into channel 44 when the contact members are moved into operative assembly with their respective mating surfaces in closely-spaced opposition.

Another feature distinguishing the modified embodiment consists of the provision of a pair of parallel, longitudinally-extending inert gas passages in each of the contact members 20, 22. Thus, with reference to FIGS. 9 and 10, contact member 20 contains a pair of parallel longitudinally extending inert gas passages 102, 104 in lieu of the single passage 62 of the corresponding contact member of the first described embodiment. Adjacent to distal end of shaft portion 28, inert gas passages 102 and 104 intersect circumferential groove 58 at the junction designated 106. At the proximal end of the shaft portion, passages 102 and 104 terminate in V-shaped channel 44 intermediate its ends.

Also in correspondence with contact member 20, contact member 22, as appears in FIGS. 11 and 12, has a pair of inert gas passages 112 and 114 extending longitudinally in shaft portion 70 and terminating in channel 76 at a point intermediate its ends. At the distal end of shaft portion 70, inert gas passages 112 and 114 intersect circumferential groove 78 as shown at 116 in FIG. 11.

Figure 13:
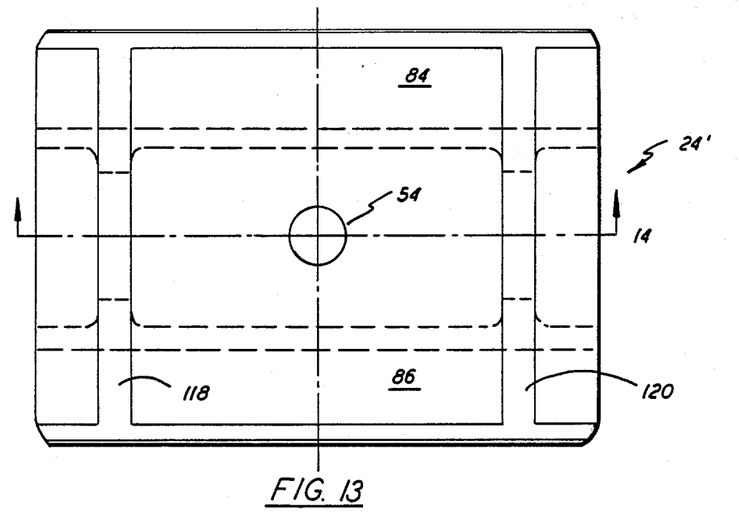
FIG. 13 is a plan view comparable to FIG. 6 showing another embodiment of the member as used in conjunction with the embodiment of FIGS. 9 to 12.
Figure 15:
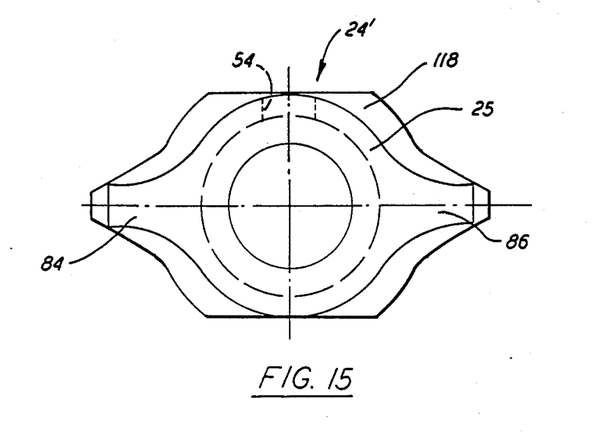
FIG. 15 is a view comparable to FIG. 8 taken on line 15—15 of FIG. 14.

In FIGS. 13 and 15, there is illustrated a modified furnace member 24' particularly configured for use with the contact members shown in FIGS. 9–12.

Figure 14:
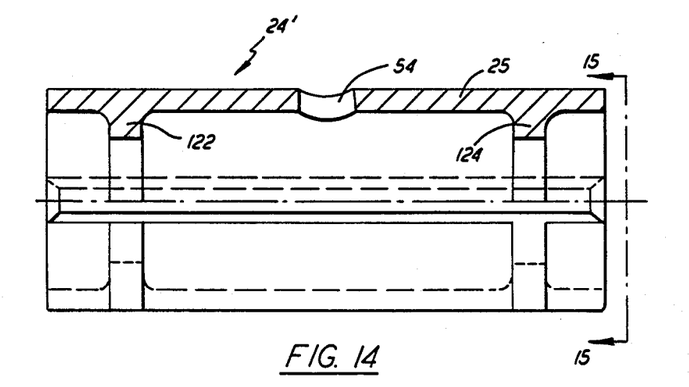
FIG. 14 is a side elevational view partially in section on line 14—14 of FIG. 13.

Furnace member 24' differs from 24 (FIGS. 6–8) in that it is formed with transversely extending reinforcing ribs 118, 120 spaced inwardly from the respective ends of its cylindrical portion 25' and joining the cylindrical portion and electrical contact ribs 84, 86. As best appears in FIGS. 13 and 14, outer reinforcing ribs 118, 120 continue as inner reinforcing ribs 122, 124 in the interior of the cylindrical portion of tubular furnace member 24'.

Reinforcing ribs 118, 120 and 122, 124 are located generally in a plane containing the longitudinal axes of inert gas passages 102, 104 and 112, 114 in contact members 20', 22' when furnace member 24' is installed in its operative position in cavity 88.

The lower electrical resistance of furnace 24' in the area of the reinforcing ribs compensates for temperature irregularities which arise from the fact that contact ribs 84, 86 are not directly contacted in the area of the inert gas passages 102, 104 and 112, 114 respectively.

The reinforcing ribs also function to permit satisfactory contact pressure of contact members 20', 22' on contact ribs 84, 86, respectively, without deforming the furnace or subjecting it to excessive loads. In the nature of things the tube is, with regard to load, less stable in the transverse direction than in the longitudinal direction.

What is claimed is:

1. In an electrothermal furnace for atomization of samples for analysis by atomic absorption spectrophotometry:
   a tubular furnace member having coplanar longitudinally extending contact ribs projecting radially outwardly from its outer surface on diametrically opposite sides thereof; and
   a pair of contact members having respective complementary mating surfaces disposed in confronting relation and coacting to define a cavity accommodating said furnace member.

2. An electrothermal furnace according to claim 1 wherein the mating surface of one of said contact members contains a recess of right rectangular parallelepiped configuration and the mating surfaces of the other of said contact members, when disposed in confronting relation to the mating surface of said one contact member, covers the recess to define said cavity.

3. An electrothermal furnace according to claim 2 further comprising:
   means defining a channel of V-shaped cross-section in the wall of said cavity which is in a plane parallel to the mating surface of said one contact member; and
   means defining a channel of V-shaped cross-section in the region of the mating surface of said other contact member which covers said recess, and extending parallel to said first V-shaped channel, said channels being adapted to receive and make electrical contact with the respective contact ribs of said tubular furnace members when installed in said cavity and the mating surfaces of said contact members are in confronting relation.

4. An electrothermal furnace according to claim 3 further comprising:
   means defining coaxially aligned bores in opposite walls of said recess perpendicular to said one wall parallel to said mating surfaces; and
   means defining at least one inert gas passage in said one contact member terminating in said one wall of the recess and at least one inert gas passage in the other contact member terminating in said region of the mating surface thereof.

5. An electrothermal furnace according to claim 4 wherein each of said contact members has a generally discoid head portion and a coaxial cylindrical shaft portion projecting therefrom, the shaft portion having a lesser diameter than the head portion, said inert gas passages extending longitudinally through the respective shaft portions, and terminating at one end in the bottom of the respective V-shaped channels.

6. An electrothermal furnace according to claim 5 wherein each of the contact members has a cooling jacket enveloping its shaft portion.

7. An electrothermal furnace according to claim 6 wherein each said inert gas passage is formed by a blind bore extending longitudinally through the respective shaft portion and terminating adjacent its distal end, each shaft portion containing a circumferential groove adjacent said distal end in flow communication with the adjoining inert gas passage.

8. An electrothermal furnace in accordance with claim 7 wherein the termination of the inert gas passages adjacent the head portion a contact member is at the mid-point of the respective V-shaped channels.

9. An electrothermal furnace in accordance with any one of the preceding claims 3 to 6, having transversely extending reinforcing ribs joined to the tubular furnace and the electrical contact ribs.

10. An electrothermal furnace in accordance with claim 9 characterized in that the inert gas passages terminate at the bottom of the respective V-shaped channels in the area of the reinforcing ribs.

11. An electrothermal furnace for atomization of samples for analysis by atomic absorption spectrophotometry comprising:
   (a) a generally tubular furnace member having a hollow cylindrical body portion and, projecting radially outward from its outer surface on diametrically opposite sides, a pair of coplanar electrical contact ribs extending along the entire length of the body portion;
   (b) first and second contact members each having a generally discoid head portion and, coaxially extending from one face thereof, a cylindrical shaft portion of lesser diameter than the head portion, the respective other faces of the head portions constituting mating surfaces adapted to be disposed in confronting relation;
   (c) means defining a recess in the form of a right rectangular parallelepiped in the mating surface of the first contact member, the second contact member when placed with its mating surface in confronting relation to the mating surface of the first contact member, coacting with said recess to define a cavity for accommodation of said tubular furnace member; and
   (d) means defining a channel of V-shaped cross-section in the wall of said cavity which is in a plane parallel to the mating surface of said first contact member and a comparable channel in the region of the mating surface of the second contact member which forms a wall of said cavity, said channels being parallel and adapted to receive and make electrical connection with the electrical contact ribs of said furnace member.

* * * * *